(12) United States Patent
Sarkis, Jr. et al.

(10) Patent No.: US 8,534,549 B2
(45) Date of Patent: Sep. 17, 2013

(54) NETWORK FOR BLOOD PRESSURE DATA MANAGEMENT AND RECHARGEABLE SMART CARD

(75) Inventors: Frederick W. Sarkis, Jr., Rochester, NY (US); Joseph O. Sarkis, Vancouver (CA); Lisa Goodwin, Penfield, NY (US)

(73) Assignee: Pharmasmart LLC, Rochester, NY (US)

( * ) Notice: Subject to any disclaimer, the term of this patent is extended or adjusted under 35 U.S.C. 154(b) by 34 days.

(21) Appl. No.: 12/994,218

(22) PCT Filed: May 26, 2009

(86) PCT No.: PCT/US2009/045141
§ 371 (c)(1),
(2), (4) Date: Nov. 23, 2010

(87) PCT Pub. No.: WO2009/143508
PCT Pub. Date: Nov. 26, 2009

(65) Prior Publication Data
US 2011/0073644 A1    Mar. 31, 2011
US 2013/0056536 A9    Mar. 7, 2013

Related U.S. Application Data

(63) Continuation-in-part of application No. 12/196,021, filed on Aug. 21, 2008, now Pat. No. 8,061,594, which is a continuation-in-part of application No. 11/502,738, filed on Aug. 11, 2006, now Pat. No. 7,438,223.

(60) Provisional application No. 60/708,125, filed on Aug. 12, 2005.

(51) Int. Cl.
| G06F 17/00 | (2006.01) |
|---|---|
| G06K 5/00 | (2006.01) |
| G06K 7/00 | (2006.01) |
| G06K 15/00 | (2006.01) |
| G06K 19/00 | (2006.01) |
| G06Q 10/00 | (2012.01) |
| G06Q 50/00 | (2012.01) |

(52) U.S. Cl.
USPC ........... 235/382; 235/375; 235/380; 235/383; 235/435; 235/487; 705/2; 705/3

(58) Field of Classification Search
USPC ................. 235/375, 380, 382, 383, 435, 487; 705/2–3
See application file for complete search history.

(56) References Cited

U.S. PATENT DOCUMENTS 6,283,369 B1    9/2001    Kurokawa et al.
6,378,073 B1    4/2002    Davis et al.
(Continued)

FOREIGN PATENT DOCUMENTS

KR    1020050018323 A    2/2005
KR    1020070102639 A    10/2007

OTHER PUBLICATIONS

ISA/KR, International Search Report of prior International Application No. PCT/US2009/045141 dated Jan. 1, 2010, total 4 pages.

*Primary Examiner* — Michael G Lee
*Assistant Examiner* — Laura Gudorf
(74) *Attorney, Agent, or Firm* — Hiscock & Barclay, LLP; Thomas R. Fitzgerald (57) ABSTRACT

Enabling the management of biometric data, including and not limited to blood pressure readings taken on automated kiosks, which is stored on personal Smart Cards and synchronized to a database via a secure network. Also, enabling the providers of automated blood pressure readings, such as pharmacies, corporate work sites, health clubs and other customers, to charge a fee for the long-term use of a memory card to record non-invasive physiological test data and make the data available for health consultations. In an automated blood pressure system with one or more memory-card interface devices, a custom-formatted end-user memory card keeps track of the user's non-invasive physiological test data, and a recharge memory card controls the provider's recharging of the end-user memory card after the end-user memory card expires. The contents of the recharge memory card are updated in order to track its use by the provider of the readings.

12 Claims, 8 Drawing Sheets

(56) References Cited

U.S. PATENT DOCUMENTS

| | | |
|---|---|---|
| 6,524,240 B1 | 2/2003 | Thede |
| 6,563,596 B1 | 5/2003 | Narushima |
| 2004/0117309 A1* | 6/2004 | Inoue et al. ............... 705/50 |
| 2006/0020517 A1* | 1/2006 | Brooks et al. .............. 705/26 |
| 2007/0057041 A1 | 3/2007 | Sarkis et al. |
| 2007/0231846 A1* | 10/2007 | Cosentino et al. ......... 435/14 |

* cited by examiner

NETWORK FOR BLOOD PRESSURE DATA MANAGEMENT AND RECHARGEABLE SMART CARD

This application is a continuation-in-part of U.S. patent application Ser. No. 12/196,021, filed Aug. 21, 2008 and now U.S. Pat. No. 8,061,594, issued Nov. 22, 2011, which is a continuation-in-part of U.S. patent application Ser. No. 11/502,738, filed Aug. 11, 2006, now U.S. Pat. No. 7,438,223, issued Oct. 21, 2008 which is a regular utility patent claiming the benefit of U. S. Provisional Patent Application Ser. No. 60/708,125, filed Aug. 12, 2005.

BACKGROUND

The embodiments of the invention relates to a network that uses machine readable cards, including and not limited to Smart Cards, for authorizing access to one or more controlled resources such as blood pressure test machines, and for the management of biometric data, including and not limited to blood pressure, stored on the smart cards and on a secure network.

SUMMARY

The embodiments of the invention described in this patent show, in their broader aspects, systems and methods for authorizing access to controlled resources. One particular resource is a non-invasive physiological test machine, such as a blood pressure machine. Other controlled resources are access to passage on a transit system, renting, leasing or borrowing articles such as vehicles, machines, equipment, DVDs, video tapes and books, or renting a hotel room or a house.

One embodiment is a system that uses machine readable cards, such as Smart Cards, card readers, displays, and transmitters for controlling access to one or more controlled resources via a public wide area network and a remote database. The machine readable cards carry a unique code and data that represent one or more or an unlimited number of authorized uses of the card over a limited or unlimited period of time of use. Card readers are located at locations of the controlled resource. The card must be swiped or inserted into the card reader by the user to gain access. The card readers read the unique code on the card to make sure it is an authorized card. The card readers also read the remaining number of authorized uses and the time of authorized use of the card. If the requested access is within the authorized period of use and the card has at least one authorized use remaining, the user is permitted access to the controlled resource. For example, if the controlled resource is a blood pressure machine, the user is allowed to operate the machine to take and record his or her blood pressure. If the controlled resource is an automobile, the user is allowed access to the automobile (e.g. the car door opens) and operation of the automobile. However, if there are no authorized uses remaining or the authorized period of use is expired, the user is denied access. The location of the controlled resource or the controlled resource itself has a display. The display is coupled to a card reader and responsive to the card reader for showing the number of remaining authorized uses of the card and the expiration date of the authorized period of use. At each location or on each controlled resource there is a transmitter that is coupled to the controlled resource and to the wide area public access network, such as a public telephone network or a computer network or any combination thereof. The network is also connected to a remote database. The transmitter sends data representative of the location of the card reader, the use of the controlled resource and the time of use of the controlled resource via the network to the remote database, through a Network Service Interface. As used in this patent, the term "network service interface" includes and is not limited to one or more computers, such as servers or work stations. Each network interface service facilitates communication between a private network operated by a receiver company and one or more sending entities which send data or inquiries to the receiver company. The data bases operated by the receiver company may be a single database with multiple fields or databases segmented by country, customer or another field. A further database may hold administrative data and statistics about the system and the data in the databases. Data and/or inquiries are transmitted to the receiver company from a variety of sources, including and not limited to the access controlled resource, the general public who may have limited access to data, information companies that mine data in the databases, and partners of the receiver company who assist in providing the access controlled resource. The receiver company has data bases that hold information received from a number of transmitters, including an not limited to about or generated by the transmitters such as local, restricted resources, and local, restricted resources, the general public, health information entities, and enterprises operated by or affiliated with the company that operates the databases. One or more of the network interface services may be specially adapted or configured to communicate with one but not all of the transmitters. For example, one network interface service may be adapted to communicate with the access limited resource, while another service communicates with the general public via the Wide World Web. Still other network services may be particularly adapted to communicate with data mining companies and still other services communicate with partners. Each of the network interface services receives transmissions and queries from one or more of the transmitters via a private or public wide area network and records data corresponding to the use of the controlled resource in accordance with the unique code of each card. The transmitter may also send results of use of the controlled resource, such as blood pressure readings, for storage in a file associated with the unique code on the card.

Other embodiments of the invention provide systems, machines and methods that use the Smart Card, the network, the controlled resources and a world wide web based application that provides a user interface to the database to interconnect patients, their doctors, pharmacists, hospitals and other medical service personnel. Each Smart Card has a unique code in the form of numeric or alpha-numeric characters. The user's name is not imprinted on the card. Instead, the user secures the card by logging into a database using the unique code on the card. The user is then prompted to verify the unique code by entering it a second time. The user may be asked to answer one or more security questions and/or establish a personal identification number (PIN). The login does not request the name or other information that could be used to identify the individual user. The security information and/or PIN, if required, are associated with the code appearing on the card and with a file in the database that corresponds to the code. When the user inserts a card into a machine or kiosk, if the card is a valid card and has authorized uses in an authorized time period, the machine operation is enabled. The machine, for example, a blood pressure machine such as the PharmaSmart Model PS-2000, takes a blood pressure reading and uploads the reading data to the remote database and into the file, which bears the code of the Smart Card. If the kiosk is off line or otherwise unconnected to the database, the Smart Card stores the readings until the next time the user takes a reading at a kiosk that is online. At that time, the stored data on the card is uploaded and stored in the coded file on the database.

As part of the card manufacturing process, a unique alphanumeric base 23 code is programmed into the memory of the Smart Card, and a matching code is printed on the card itself. This code is 9 digits long: for example WEG-AAA-AKG. The blood pressure kiosk that accepts the Smart Card is connected to a database. The World Wide Web application, network service interface and database may each be at any location. In one embodiment, the network service interface and database is located on one or more networked computers that is connected to the World Wide Web or other public or private network. The kiosk communicates through the network service interface to transmit readings and related metadata associated with the unique access code on the smart card. The network interface services then processes this data and update the related database data associated with the unique access code with any new reads found on the smart card. Each of these readings will be stored in a secure database, and will be identified by the card's unique alphanumeric code.

This system and method allow the user, or the user's healthcare provider, to access the blood pressure data via the internet using a specially designed graphic interface (website) that allows the data to be presented, viewed, filtered and printed in informative and educational ways. The only process to view the data is to enter the nine digit number into a "login" page on a website that is connected to the database. The user may permit others, such as physicians, pharmacists, nurses, to see the user's data by giving them the PIN or security information. Since there are no names associated with the unique ID's, the process is fully HIPPA compliant.

This system is efficient and secure. It allows the database operator to identify who issues the card because the first three characters identify the entity who issues the card. For example, a card bearing the code AAP-XXX-ZZZ, where the first three characters identify the organization who issues the cards. For example, the characters "AAP" may stand for the All American Pharmacy, which is a hypothetical chain of pharmacies distributed throughout the U.S.A. However, other, non-commercial organizations, such as the National Institutes on Health, could issue Smart Cards to participants in a blood pressure studies and use the results of the uploaded readings to conduct one or more blind studies. Other organizations include independent pharmacies, hospitals, nursing homes, etc. This allows the distributor of the card to provide custom branding on their web-site interface. When this particular user types the card code into the "log-in" website, the website is an AAP-branded "personal health record" site. This system also enables exclusivity by card issuer. For example, the blood pressure machines can be configured to accept only cards with codes bearing the first three characters "AAP". Therefore, Smart Cards issued by another retailer or organization could not be utilized in the blood pressure machines located in All American Pharmacies.

The Smart Card and its database system have many applications for a variety of issuers. Its connectivity via the Web will be extremely useful for clinical trials that require the aggregate data analysis of the blood pressure of large groups of people over long periods of time. Alternatively, an employer could issue Smart Cards to its employees to acquire data on how the employer's wellness program is working.

The Smart Card and its database system may be used in conjunction with other existing or expected medical records systems, such as Electronic Medical Record (EMR) software companies (physician patient care software), MTM (Medication Therapy Management software—used by pharmacies), Diabetes Diagnostic Companies (Roche, Bayer, and Lifescan), and web based Personal Health Record companies such as Microsoft HealthVault and Google's new personal health record program. Data collected from the Smart Cards may also be mined by geographic location.

The system can also be linked to personal communication devices, such as Apple's IPhone, RIM's Blackberry, Google's Android, Palm's Pre, Microsoft's Windows Mobile or other cellular phones via custom software applications that enable secure access to specific end user data similarly to the PC based web application described above.

The method, apparatus and system of the disclosed embodiments rely upon automated blood pressure (ABP) machines and other types of non-invasive medical self-monitoring equipment, e.g., weight scales, automated glucose monitors, cholesterol monitors, blood oxygen monitors. These machines are either purchased or leased by pharmacies, corporate work sites, health clubs and other customers. For the purpose of this discussion, these customers will be referred to as "Locations".

The Locations provide ABP and other medical self-monitoring machines as a service to their customers, employees, members, etc. For the purpose of this discussion, we will refer to these customers, employees, and members using the ABP or other medical self-monitoring machines as the "End User". Such Locations often offer the End User the option to use a Smart Card to record and track their blood pressure history over time.

As used in this patent, the term "memory card" includes any device that is generally the size of credit card (2"×3.25") with power, ground, input and output ports or terminals and an array of memory cells arranged in rows and columns. Such memory cells are typically made of flash memory that is static memory devices that retain their information when electrical energy to the card is removed. Smart Cards include memory arrays of flash memory cells and have a microprocessor or other control or logic circuitry. One purpose of the microprocessor or other circuitry is to provide security for the data on the card. Such Smart Cards have encryption and decryption keys or stored programs that secure the card from unwanted access.

Each time the End User uses the memory card or Smart Card in the machine, the blood pressure reading, pulse rate, and the date of the measurement are recorded on the card. The ABP machine then prints out a history of the End User's most recent results (as many as 10 results), and provides a calculated average blood pressure and pulse rate for the End User. Similar monitoring, data collection, data compilation, and data presentation opportunities exist for other forms of medical self-monitoring equipment. A printed history of the End User's most recent results for any such monitoring process is important as it provides the End User with information to share with physicians, pharmacists, and other health care professionals. Recorded ABP information assists the health care professional in evaluating the End User's blood pressure history and the effectiveness of any End User hypertension control program. Recorded weight, glucose levels, cholesterol levels, blood oxygen levels, and other records of medical monitoring for the End User can likewise assist health care professionals in their care of that End User.

The embodiments enables the providers of automated blood pressure readings and other non-invasive physiological test data, such as pharmacies, corporate work sites, health clubs and other customers, to charge an annual fee for the use of a memory card or Smart Card to record the non-invasive physiological test data and make the data available for health consultations.

A kiosk, machine or other controlled resource may have an operating program. That program comprises software is installed, for example, in a computer of an automated blood pressure system or other medical self-monitoring system. The software may be accessed with one or more memory card or Smart Card interface devices, uses a custom-formatted end-user memory card for keeping track of the user's non-invasive physiological test data and the dates these readings were taken. The software also provides the option to control uses of the card by requiring the card be reauthorized for further uses beyond the initial authorized number of uses.

The embodiments of the invention may be applied to other, non-medical systems for recording readings and verifying usability.

BRIEF DESCRIPTION OF THE DRAWINGS

FIGS. 2, 5, 6 are a flow chart of steps for creating a User Smart Card.

DETAILED DESCRIPTION OF THE EMBODIMENTS

Figure 1:
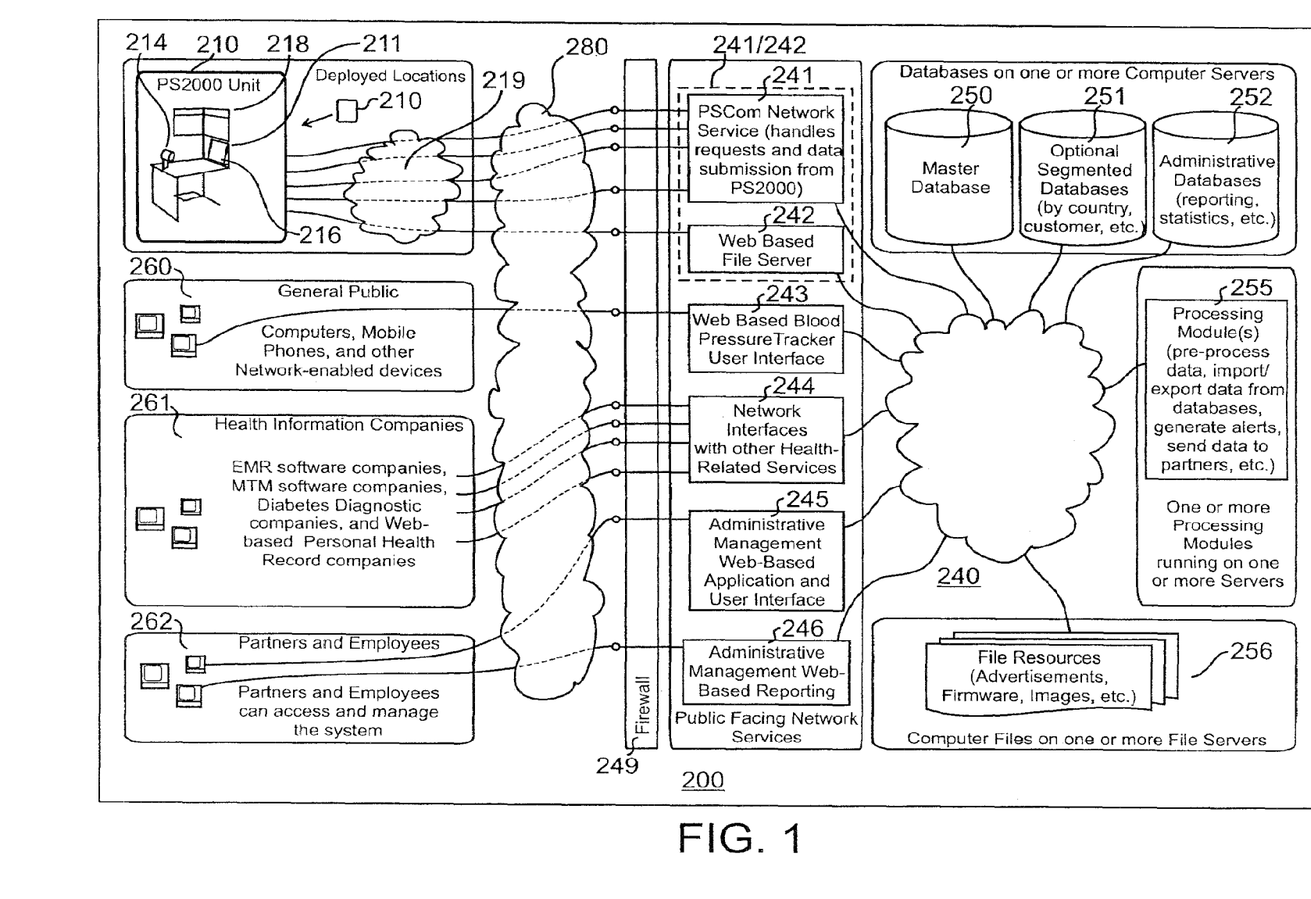
FIG. 1 is a schematic view of network using a secure User Smart Card.

Turning to FIG. 1, there is shown a schematic of a system 200. Kiosks or machines 210 (those terms are interchangeable) are installed at one or more deployed locations that are controlled by a Partner. As used herein, a Partner is an entity or enterprise that engages with the PharmaSmart (or a similar manufacturer or database operator) to issue Smart Cards and permit Smart Card Users access to the kiosks. Such kiosks are found at pharmacy or any business or enterprise open to the public. The 210 is a controlled resource for recording physiological data, in particular blood pressure readings, glucose readings, etc. The kiosk 210 has a card reader 211 for accepting and reading data on and storing data in a machine readable Smart Card 201. Local display 218 shows the current and/or recent readings. One or more control buttons 216 are used to actuate the blood pressure cuff 214. Arrows 215 indicated the cuff inflating and deflating. The card 201 may be used to initiate operation of the machine 210.

The machine 210 has a transmitter, modem or other device that is connected to a partner private network 219. The partner private network may include one or more kiosks operated by a partner who has machines at one or more locations. The partner private network 219 is coupled to a wide area public network 280, such as the Internet. A data collection private network 240 is also connected to the public network 280 via a firewall 249 which has an integrated collection of security measures designed to prevent unauthorized electronic access to the data collection private network 240. The machine 210 may gain access to the data collection private network 240 through the security checks made by the firewall 249 and then through one of two network interface services (NIS) 241, 242. In general, NIS 241 handles requests and data submissions, e.g., blood pressure readings, from machines 210 to the data collection private network 240. NIS 242 is a web-based server that parses data for partner reports. Upon completion of a non-invasive blood pressure (NIBP) test, data from the reading and/or other data stored on the card 201 are uploaded to the networks 219, 280, 240 for transmission to and storage in a database 250.

The card 201 controls access to the machine 210 and/or controls access to a remote database 250 through a network interface services 241 or 242. The machine 210 is configurable to not read blood pressure unless the card is an authorized card and has been inserted, read and validated. In that case, after the card is validated, the user initiates operation of the machine 210 by pressing a control button 216. The results of the test are shown in the display or printed. The results may also be stored on the card 201 and transmitted to the remote database 250 via the network interface service 241. In an alternate embodiment, the machine may work, but readings of the user's blood pressure will not be transmitted to the remote database or stored on the card.

The data collection private network 240 has one or more data bases 250, 251, 252 disposed on one or more servers. Those skilled in the art understand that all data could be held in one database on one server. However, those skilled in the art also understand the advantages of partitioning databases among one or more servers in order to spread the load of traffic over several servers and thereby provide overall faster system response. For example, a second database 251 may hold data by country or partner. A further database 252 may be for administrative purposes and hold reports and statistics. The network 240 has processing modules 255 that import and export information and send data to partners and users. Other file resources include, for example, advertisements, firmware, images, etc that may be accessed by partners for use at the deployed locations.

The network 240 provides different network interface services (NIS) for handling communications between the network 240 and locations, users, trusted sources and partners. For example, NIS 243 is a web-based blood pressure tracker. It interfaces a user to the user's data so that the user may track recorded blood pressure readings from any personal computer or network enabled device. 260. NIS 224 interfaces with health information entities to provide access to the databases 250-253. NIS 246 interfaces partners and their employees for administrative management web-based reporting. The respective NISs 241-246 receive data from the various sources 210, 260, 261 and 262, parse the data into predetermined fields, and distribute the data to other parts of the network as required.

The data in the database 250 are accessible to the user via a personal computer, mobile phone, or other network enabled devices 260. One or more trusted sources, such as the user's physician, pharmacist, or a health agency 261 may have limited or unrestricted access to one or more user records in the database 250. Examples of such health agencies include and are not limited to insurance companies, electronic medical record keepers, patient card monitoring entities, and web-based personal health records companies such as Microsoft Health Vault and Google's personal health records web site. Further examples include the National Institutes of Health, medical data mining agencies or any other health agency that is conducting a clinical study. The data may also be given to the user on a local display 218. The display may show the most recent reading along with a history of a selected number of the most recent readings. As a further option, the machine 210 may be connected to a printer (not shown) and the current test results and the most recent results displayed on the screen can be printed for the user.

The Smart Card 201 bears an identification code, for example, AAP-1B5-6C7. The first three characters in the code indicate the card was issued by the All American Pharmacy. The card 201 does not bear the name of the user and the All American Pharmacy does not record the identity of the user. The card 201 is given to the user free of charge or for a nominal fee, e.g. $1.50. As such, only the user of the card may associate the data stored in database 250 with the identity of the user. No other party has access to the identity of the user unless the user permits such access.

The user does not have to take any further action to record data to the database 250. Each time the user inserts the card 201 into the kiosk 210, the readings from the card are uploaded to the database 250 via the network 219 or 280. The data from card 201 are stored in a file identified by the code AAP-1B5-6C7 which appears on the face of the card.

In order to gain access to the stored data, the user may log into the web based network interface service 243, which is a front end user interface to the database 250. Upon login, a conventional security program may ask for the user's PIN, or ask a security question. If this is the first time the user is logging in, the system may ask the user to establish a PIN and/or record answers to one or more security questions, such as "What was your mother's birth (maiden) name." The user is free to share his or her unique access code, or PIN or security information with other trusted sources, such as a physician, a pharmacy, or a clinical agency 261.

The card does not carry the identity of the user. The invention has additional embodiments usable in non-medical contexts for any application that gathers, stores, and recalls a limited number of data values on a rechargeable basis as described hereinabove.

One such application is transit systems, wherein an embodiment charges a User Smart Card with travel credit increments deductible at each stage of a journey on a transit system. At each stage of the journey, the embodiment notes the time and location of the user's entry for travel, and deducts one or more credit increments as appropriate for the stage on which the user is embarking. The user may afterwards obtain from the Smart Card a record of travel for business or evidentiary reasons.

Another application is a library or other lending system, wherein the embodiment charges a User Smart Card with lending credit increments deductible by the user when borrowing a book, film, music score, or other item of rental or lease of goods or equipment. Different items borrowed may result in different numbers of credit increments being deducted. The embodiment stores the time and date of lending or rental and the time and date of return of the item on the User Smart Card.

In its basic embodiment, a network uses an apparatus and a process, developed initially for the PharmaSmart Model PS-2000 blood pressure machine and similar machines made by others. The PS-2000 is equipped to use blood pressure Smart Cards to store blood pressure readings for the End User. It is likely that millions of these blood pressure Smart Cards will eventually be in circulation in North America and in other parts of the world. The embodiment provides the option for Locations to: 1) generate additional revenues by charging the End User an annual fee for use of the Smart Card, and 2) provide End User with at least one annual blood pressure consultation.

Figure 2:
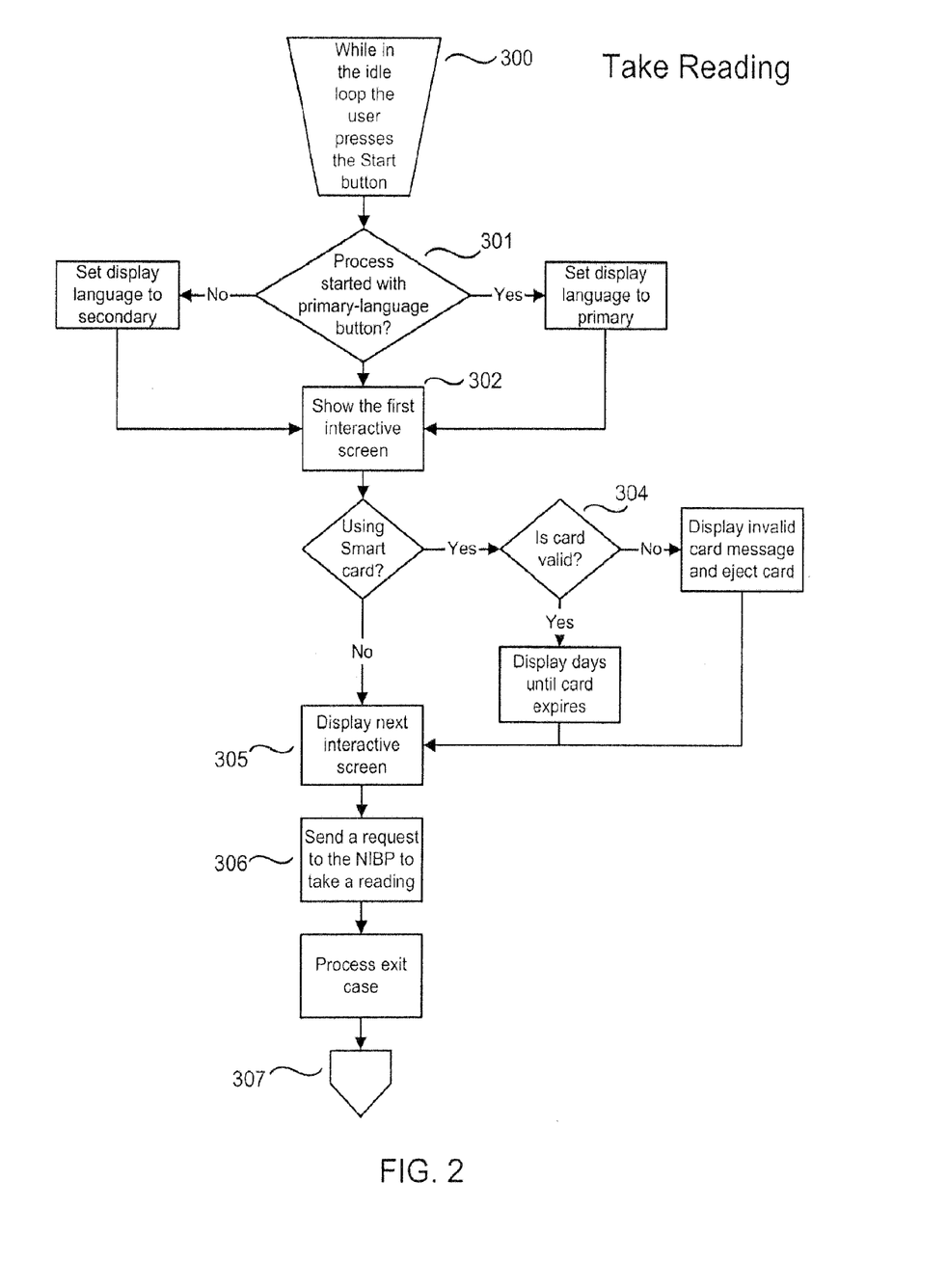
FIGS. 2, 3, 4 are a flow chart of steps for using the User Smart Card
Figure 3:
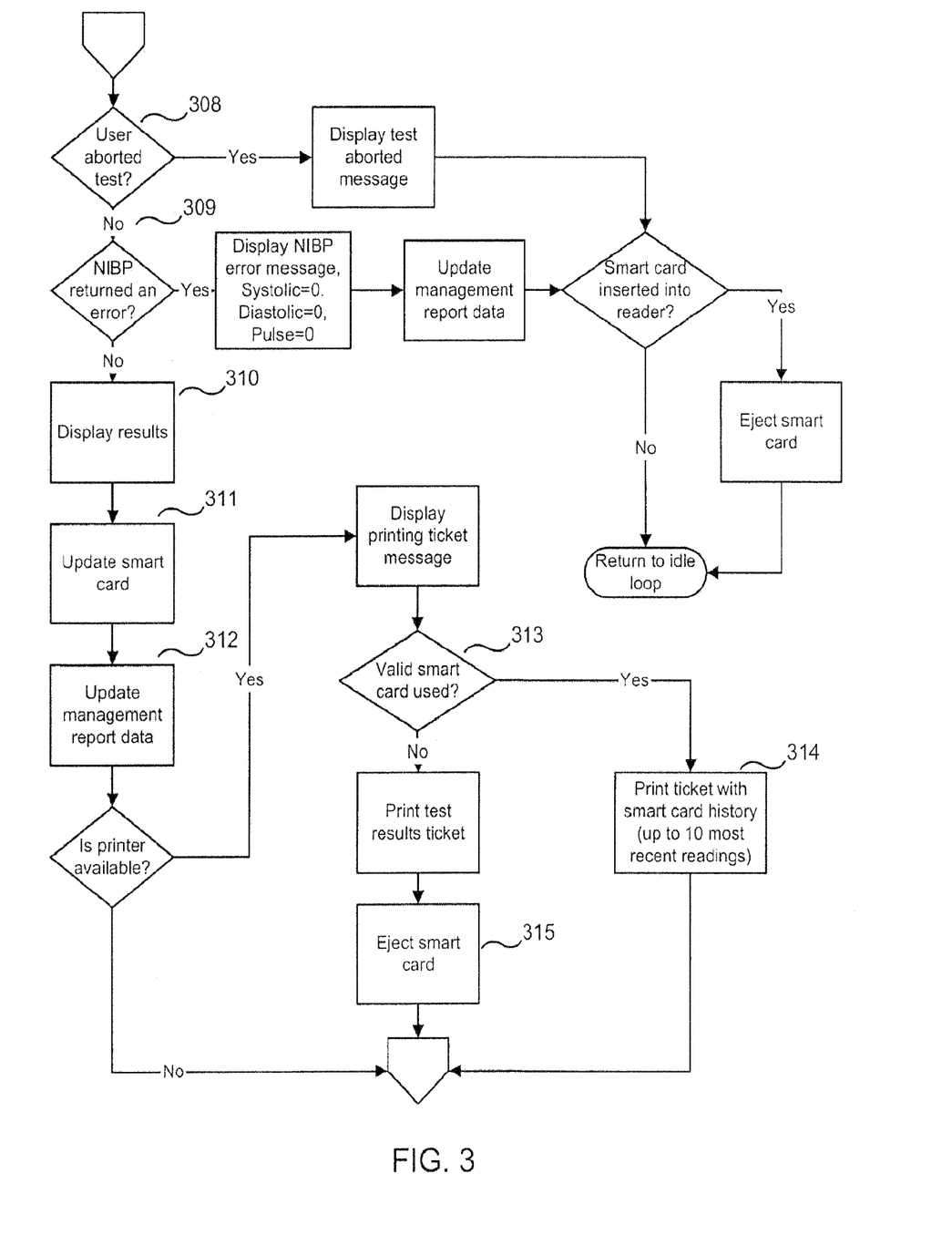
Figure 4:
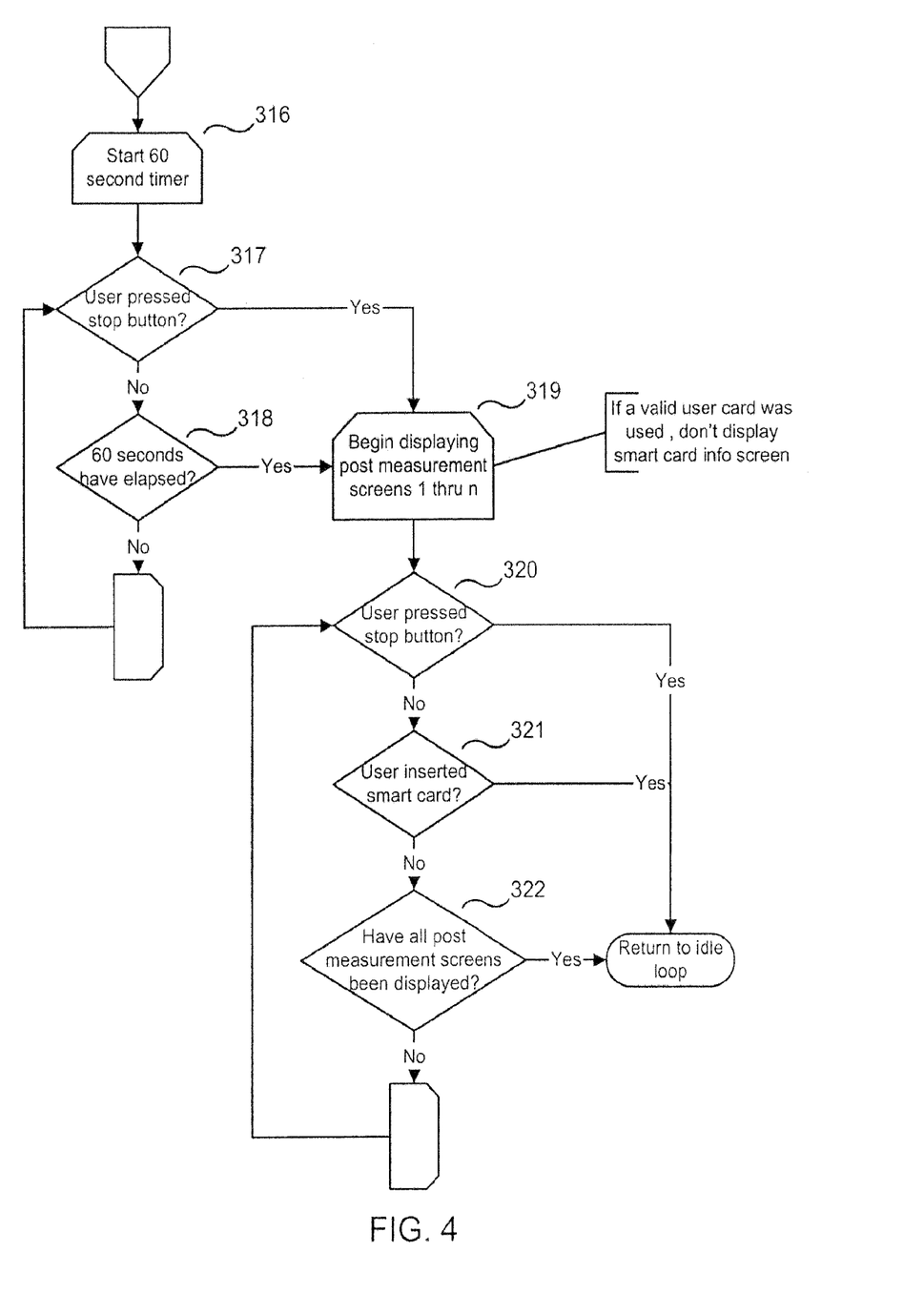

Turning to FIGS. 2-4 there is a basic flow chart of steps for operation of the kiosk 210 using a Smart Card. In step 300, the user has inserted the card into a card reader and then presses the Start button on the machine 210. The program checks for the primary language of the user 310 and then shows the use a first interactive screen 302 on the display 218. Step 304 checks to see if the card is a valid Smart Card. If it is, the program advances to step 305 and displays the next interactive screen. At step 306, the user requests a reading and the machine 210 inflates the cuff and gradually reduces the pressure in the cuff to take a non-invasive blood pressure (NIBP) reading in step 307. Unless the user aborts the test 308 or there is machine error 309, the reading is displayed on the machine's display 310, stored on the card 311, and sent 312 to the master database 250 in the form of a management report. If a printer is available the card is validated a second time 313 and a ticket is printed with a set of the most recent readings, for example, the last ten readings 314. Then the card is ejected 315. Next, the machine enters a wait state routine (steps 316-322) to see if the user wants to take another reading. Upon completion of the wait state routine with no further user input, the machine returns to its idle loop 300.

In an alternate embodiment of the invention, the card is not equipped with a memory and/or microprocessor, but is simply a card with a machine readable code. The user has a PIN or unique access code associated with the card, but the user's name appears nowhere on the card. If the card is lost or stolen, the user's data on the network is secure. Even if one obtains the data associated with the card, the identity of the card holder is unknown to the finder or thief.

The kiosks 210 may use an optional reauthorization (hereinafter "recharge") feature. As used herein, the terms "reauthorization" and "recharge" have the same meaning. The term "recharge" is not used in the sense of a rechargeable battery that can receive and hold electrical energy. Instead, the term "recharge" is intended to indicate a date after which the Smart Card will no longer work for its intended purposes. With this feature, the first time the End User uses the Smart Card in the machine; it electronically "stamps" a recharge (i.e. expiration) date into the Smart Card. The recharge date is a fixed or variable date, but preferably is one (1) year from the date of first use in the machine. This means the End User has a full year of use of the Smart Card before it will require a recharge. If the card is not recharged by the recharge date, it will no longer work in the machine.

Many retailers want branded cards that drive the user back to the same retailer. For example, a regional or national pharmacy chain would like the user to always visit a location of the retail pharmacy in order to use the card. This system also enables exclusivity by card issuer. For example, the blood pressure machines can be configured to accept only cards with codes bearing the first three characters "AAP". Therefore, Smart Cards issued by another retailer or organization could not be utilized in the blood pressure machines located in All American Pharmacies. In addition, the retailer may set limits on the number of times the card may be used. By requiring the user return to the retailer to recharge or reauthorize the card, the system would induce the user to return to one of the establishments in the retailer's chain in order to reauthorize the card for additional uses. The retailer may reauthorize the card free of charge or for a nominal fee. In either case, the card is reauthorized with a new set of credits for its use. At any time, the Location may purchase recharge credits directly from manufacturer of the ABP machine. These credits are loaded onto a unique "Recharge Smart Card", and shipped directly to the Location. Upon the End User's request, the Location personnel can use the Recharge Smart Card to recharge the End User's card for an additional year. In order to do this the Location personnel must have both the Recharge Smart Card and the End User Smart Card in hand. They then simply insert the Recharge Smart Card into the ABP machine and follow the instructions provided on the machine's display. Once completed, an updated recharge date is electronically "stamped" onto the End User Smart Card providing another time period, for example, a full year, of use of the Smart Card. Each time the Location personnel recharges an End User Smart Card, the Recharge Smart Card is debited one (1) recharge credit. Once all of the recharge credits are used, the Location personnel discards the Recharge Smart Card and, as required, may order an additional Recharge Smart Card from the ABP machine manufacturer.

The kiosk manufacturer may charge Partners a fee for each recharge credit they order, and the Partner can charge the End User an annual fee for the User Smart Card.

Figure 5:
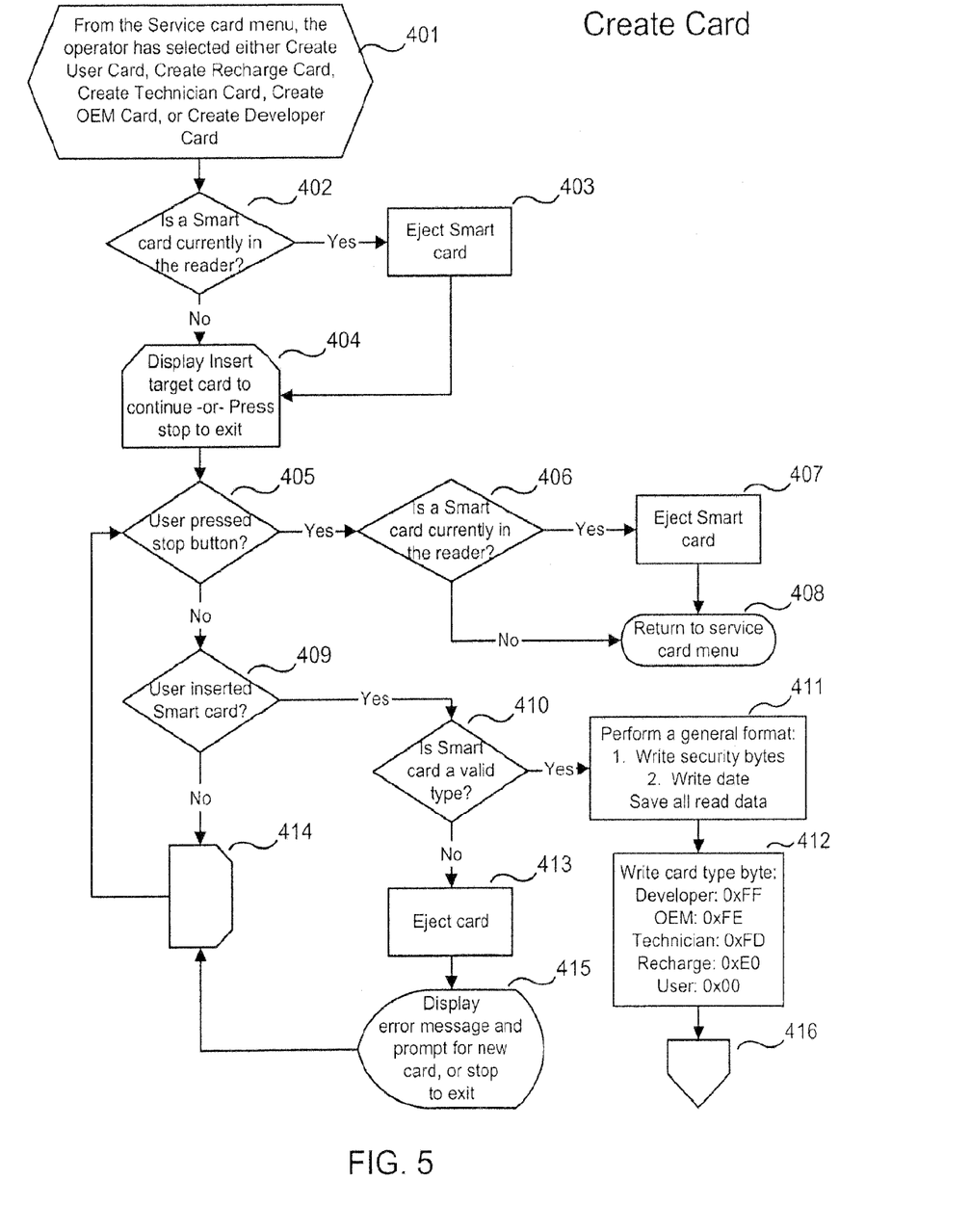
Figure 6:
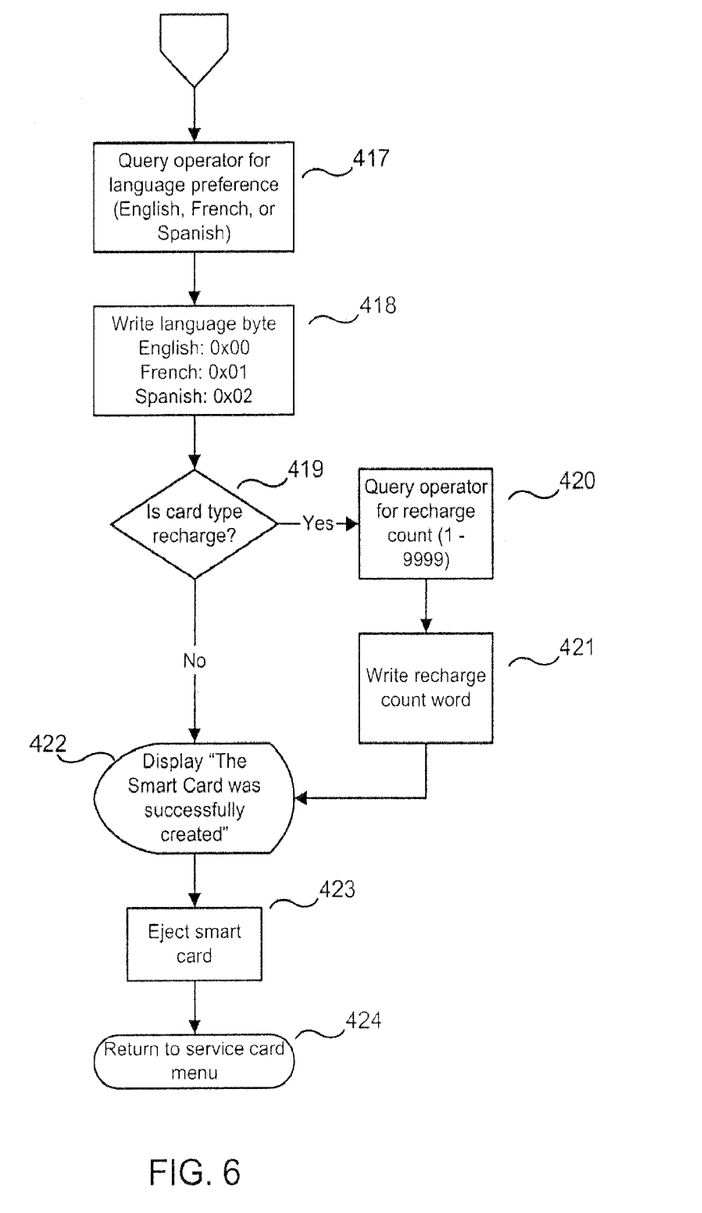

User Smart Cards are created in the machine 210 following steps 401-424 as shown in FIGS. 5, 6. The operator at a Partner location has a Service Card. When the operator places the Service Card in a reader, the menu appears with one or more selections including a selection to "Create OEM Card." The operator inserts 404 a blank OEM Smart Card into the reader. Unless the user-operator stops the operation 405, the Smart Card is evaluated to see if it is a valid type, i.e., one that is recognized and acceptable by the system. If so, the system performs a number of operations 411,412 on the card to format the card, add security bytes, and record the OEM and other administrative data. If it is not a valid card 415, it is ejected. Assuming the card is a valid card, the operator may then set the language preference 417 for the card. If the card is a Recharge Card 419, the operator is asked for its number of counts or recharges and is ejected 423.

In the alternative, the retail location may add credits to the card free of charge. As a further alternative, the retail location may authorize unlimited use of the card. In that case, the memory on the card is configured to store data on a first in, first out basis and the data on the card is always the most recent data acquired by using the card.

Figure 7:
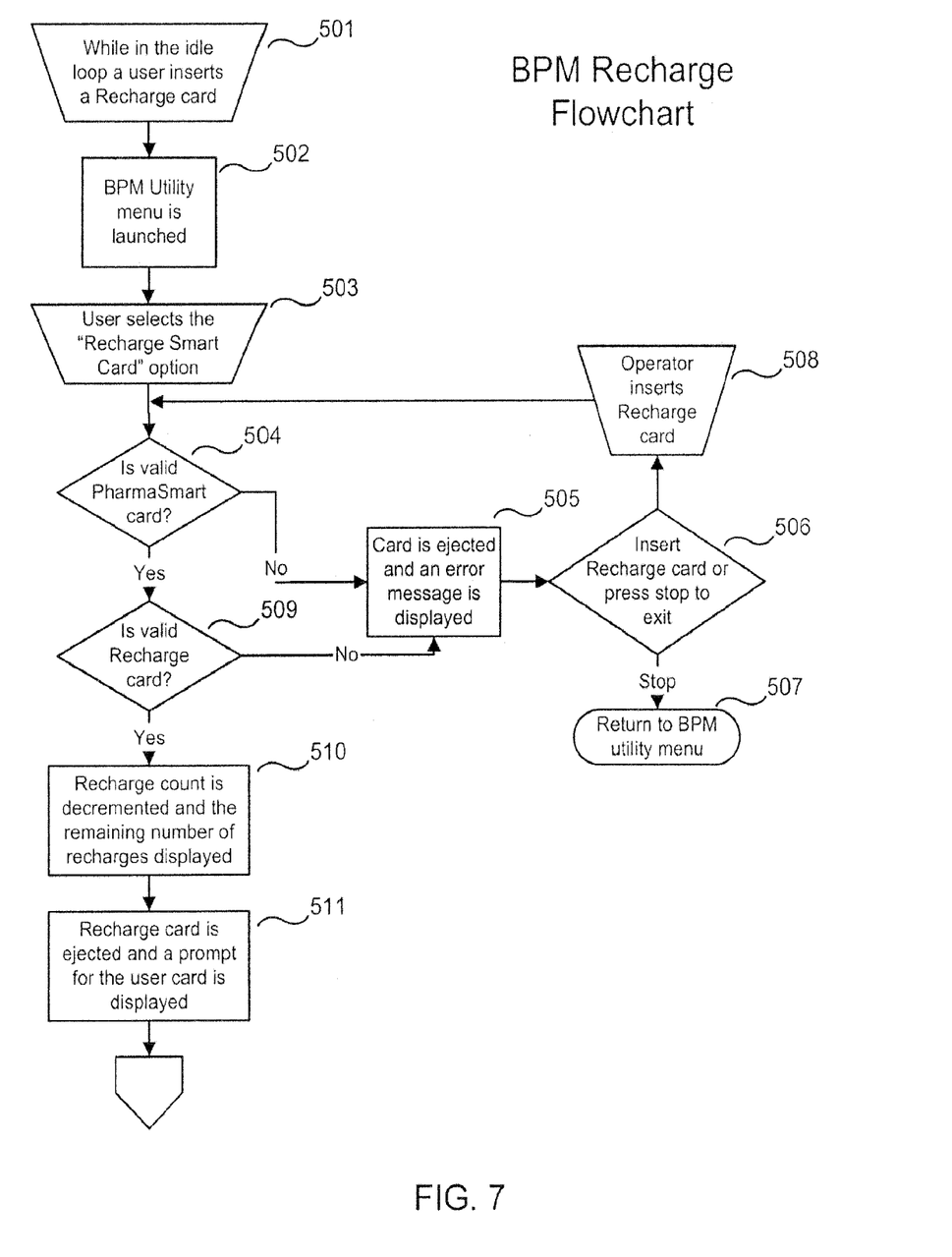
FIGS. 7, 8 are a flow chart of steps for recharging a User Smart.
Figure 8:
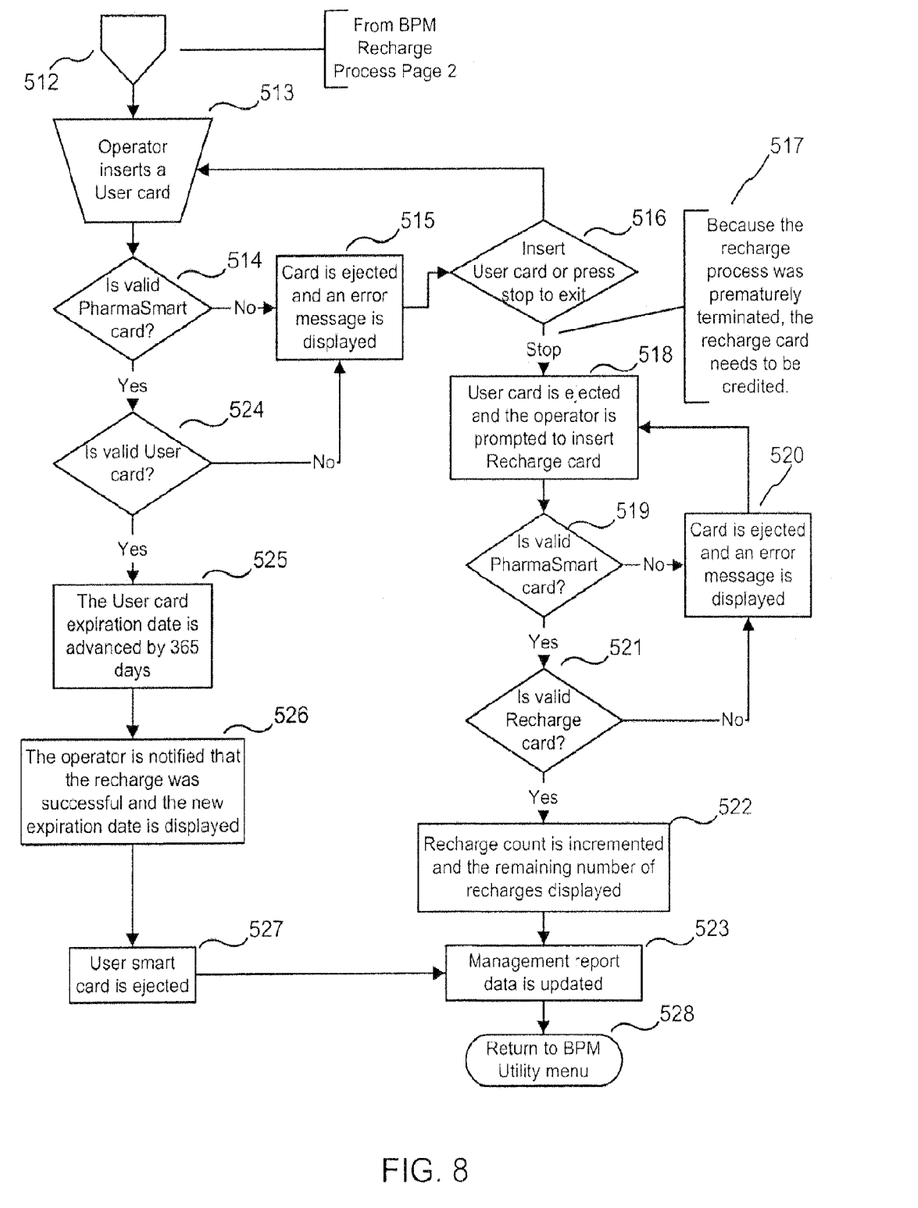

FIGS. 7-9 show a combined flow chart presenting specific software design and operational details of the Smart Card recharge process as performed using a single-port card reader. There are three overall parts of the recharge process: 1) updating the Recharge Card, 2) updating the User Smart Card, and 3) restoring the Recharge Card to an earlier state when a User Smart Card update has not been completed. Steps 501-528 are steps of the updating of a Recharge Card. The operator inserts the Recharge Card in the card reader 501. The system presents the BPM utility menu to the operator 502. The operator selects 503 the "Recharge Smart Card" option from the menu. The system reads the Recharge Card contents. If the card is not a valid PharmaSmart card of any type, the system displays 506 a message to that effect and prompts the user to use a PharmaSmart Recharge card and ejects 505 the invalid card. If the card is a valid PharmaSmart Recharge Card 509, the system decrements 510 the card's Recharge Count, and displays the number of recharges remaining on the card, ejects the Recharge Card, and prompts the operator to insert the User Smart Card 511. Once the Recharge Smart Card is decremented one credit, the User Smart Card updating process begins. The operator inserts 513 the User Smart Card. If the card is not a valid PharmaSmart card of any type, the system displays 515 a message to that effect and prompts the user to use a PharmaSmart User Smart Card. If the card is a valid PharmaSmart User Smart Card, the system advances 525 the card's Expiration Date by 365 days, or if the Expiration Date has passed, sets a new Expiration Date 365 days from the User Smart Card's update. The system notifies 526 the operator of the successful update and displays the total number of days until the User Smart Card will require another recharge. The system ejects 527 the User Smart Card. The system updates 523 its management report data, and returns to display 501 the BPM Utility Menu. During the User Smart Card update, the operator may decide that the recharge process cannot be completed. If the process is not completed, the Recharge Card and the User Smart Card are left in states that are mutually inconsistent. The Recharge Card indicates that a recharge has been done, while the User Smart Card has not been recharged. Consequently, the inconsistency should be corrected. The Recharge Card should be incremented one Recharge Credit. See step 517

At present there are three versions of the Smart Card. Version 1 may be used in the embodiments but they do not provide security for the data on the card. However, they are less expensive than the more secure Smart Cards and can store the same user data that is stored on a Smart Card. Version 2 is an encrypted Smart Card that provides added security. Version 3 is an encrypted and web-adapted smart card that a user may employ to access the Web Based Blood Pressure Tracker 243.

In a general embodiment providing for storage and analysis of non-invasive physiological test data and other medical monitoring information, the User Smart Card records values from automated equipment for reading blood glucose level, blood cholesterol level, or other testable medical parameter values. The range of testable medical parameter values expands constantly as new technologies enable rapid, reliable, low-powered monitoring techniques to be packaged and made available to an End User.

The User Smart Card records the non-invasive physiological test data that the user took over the course of a year. The user can use the User Smart Card to access this entire history at any Location, and print out the most recent 10 entries or all of them. The average of the printed entries is given with the printout. The date of each reading is also recorded on the User Smart Card and printed alongside each entry, allowing the user or a physician to identify trends in the data. Additionally, at the user's request, the data from the User Smart Card can be loaded into the computer system of a pharmacy or doctor's office, allowing health care workers quick access to the user's non-invasive physiological test data.

At a Location, the user can print out the entire history of non-invasive physiological test data stored on the user Smart Card. Additionally, at a pharmacy or physician's office this data can be submitted for a consultation on the patient's condition. When the User Smart Card is recharged, an option is given to allow the user to submit his data to a pharmacy for a consultation.

Tests now performed in a laboratory, such as blood enzyme levels for such critical markers as creatine phosphokinase (CPK), will eventually be capable of being performed properly and inexpensively in a manner similar to that now used for blood pressure monitoring. Furthermore, evaluations requiring significant analysis and processing of data, such as the classification of cardiac arrhythmias requiring medical attention, may become capable of being performed in a consumer setting as well.

Finally, numerous drugs, such as the COX-2 inhibitors, can produce varied deleterious effects on small subsets of their users. The monitoring of blood markers for adverse or allergic reactions to such drugs presents another field of application for the present invention.

To record the values captured, the embodiment substitutes different value sets and ranges for different types of reading and different sensitivity requirements. For example, readings of blood glucose levels when fasting range from the 60-100 range (excellent) to above 180 (poor), but after a meal the range rises so that the 110-140 range represents an excellent level, while above 220 represents a poor level of blood glucose (source of values: University of Massachusetts Medical School Web page concerning self-monitoring of blood glucose levels using the lancet). Ranges for different classes of monitored values are represented in the embodiments of the invention using range classifications, biasing of values, elimination of non-significant digits of precision, and other techniques well-known in the art for compressing data values for storage in limited memory space.

In a secure embodiment, the invention incorporates conventional anti-tampering hardware and software components in the User Smart Card and the Recharge Card to prevent an End User, a Location employee, or a thief from using a conventional standalone card reader to alter the contents of the User Smart Card or the Recharge Card.

In the secure embodiment, the invention applies encryption to the contents of the card, rendering the contents of the card unreadable by any process except the decryption of the encrypted values. The Location employee (for the Recharge Card) or the End User (for the User Smart Card) reads and updates the card's contents by furnishing the decryption key for the card. The specific encryption techniques used are well-known in the art and so are not described here.

Any attempt to read the card's contents using a conventional standalone card reader triggers the execution of software which breaks open one or more fuses on the card, rendering the card useless. While such measures do not prevent fraudulent misuse of the card, they make such misuse considerably more difficult.

The operation, contents, encryption, and decryptions of the embodiments of the invention's Recharge Card are the same for all classes of data to be collected.

What is claimed is:

1. A system comprising;
a plurality of cards, each card carrying a unique code and holding information associated with a legitimate custodian of the card, each card having an authorized number of uses for an authorized time period;
a remote database with a first network interface for transmitting and receiving data over a wide area network;
a plurality of card readers for reading the unique code on each card, the number of remaining authorized uses of each and the authorized time period for each card and for controlling use of non-invasive physiological test machines;
one or more non-invasive physiological test machines for performing one or more non-invasive physiological tests on the legitimate custodian of the card;
each non-invasive physiological test machine having a display for showing non-invasive physiological test results acquired by the non-invasive physiological test machines;
each non-invasive physiological test machine having a transmitter for sending data representative of the non-invasive physiological test results via the wide area network to the remote database via a network service interface; and
the remote database coupled to the network through a second network interface for receiving transmissions from the transmitter and for storing records of the non-invasive physiological test results by the unique code of each card;
wherein the cards do not carry data representative of the identity of the legitimate custodian of the card.

2. The system of claim 1 further comprising one or more computers with authority to access data in the database associated with the unique codes on the cards.

3. A system comprising;
a plurality of cards, each card carrying a unique code and holding information associated with a legitimate custodian of the card, each card having an authorized number of uses for an authorized time period;
a remote database with a first network interface for transmitting and receiving data over a public wide area network;
a plurality of card readers for reading the unique code on each card, the number of remaining authorized uses of each and the authorized time period for each card and for controlling use non-invasive physiological test machines;
one or more non-invasive physiological test machines for performing one or more non-invasive physiological tests on the legitimate custodian of the card;
each non-invasive physiological test machine having a display for showing non-invasive physiological test results acquired by the non-invasive physiological test machines;
each non-invasive physiological test machine having a transmitter for sending data representative of the non-invasive physiological test results via the public wide area network to the remote database via a network service interface; and
the remote database and said coupled to the network through a network service interface for receiving transmissions from the transmitter and for storing records of the non-invasive physiological test results by unique code number,
wherein the cards do not carry data representative of the identity of the legitimate custodian of the card.

4. The system of claim 1 wherein the cards have a memory for holding data representative of non-invasive physiological test results.

5. The system of claim 1 wherein the cards have a memory for holding data representative of authorized uses of the card.

6. The system of claim 1 wherein the cards have an authorized number of uses for an authorized time period.

7. The system of claim 6 further comprising means for authorizing further uses and for extending the authorized time period.

8. The system of claim 4 wherein the cards have security means for preventing access to or alteration of any component of the records of usage information, said security means comprising a machine readable code on the card.

9. The system of claim 1 wherein the machine conducts a blood pressure test.

10. The system of claim 1 wherein the cards comprise electronic smart cards with means for reading and writing data.

11. The system of claim 10 wherein the means for reading and writing data includes one or more of the group consisting of flash memory, optical memory, magneto-optical memory and a miniature hard disks drive.

12. The system of claim 1 wherein the display is a monitor or a printer.

* * * * *